(12) United States Patent
Flory et al.

(10) Patent No.: US 8,563,237 B2
(45) Date of Patent: Oct. 22, 2013

(54) BIOPOLYMER RESONANT TUNNELING WITH A GATE VOLTAGE SOURCE

(75) Inventors: Curt A. Flory, Los Altos, CA (US); Richard J. Pittaro, San Carlos, CA (US); Phillip W. Barth, Portola Valley, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 1279 days.

(21) Appl. No.: 10/996,846

(22) Filed: Nov. 23, 2004

(65) Prior Publication Data

US 2006/0071209 A1    Apr. 6, 2006

Related U.S. Application Data (63) Continuation-in-part of application No. 10/957,378, filed on Sep. 30, 2004, now abandoned.

(51) Int. Cl.
| | | |
|---|---|---|
| *C12Q 1/68* | (2006.01) | |
| *C12M 1/00* | (2006.01) | |
| *C12M 1/34* | (2006.01) | |
| *C12M 3/00* | (2006.01) | |

(52) U.S. Cl.
USPC .... 435/6.1; 435/283.1; 435/287.1; 435/287.2

(58) Field of Classification Search
USPC ............ 435/6, 6.1, 283.1, 287.1, 287.2
See application file for complete search history.

(56) References Cited

U.S. PATENT DOCUMENTS

| | | | | |
|---|---|---|---|---|
| 4,288,303 | A * | 9/1981 | Matson | 205/347 |
| 5,795,782 | A * | 8/1998 | Church et al. | 436/2 |
| 6,627,067 | B1 | 9/2003 | Branton et al. | |
| 2003/0039586 | A1 * | 2/2003 | Toyoda et al. | 422/98 |
| 2003/0141189 | A1 | 7/2003 | Lee et al. | |
| 2003/0211502 | A1 | 11/2003 | Sauer et al. | |
| 2004/0144658 | A1 | 7/2004 | Flory | |
| 2005/0202446 | A1 * | 9/2005 | Yang et al. | 435/6 |

FOREIGN PATENT DOCUMENTS

| | | |
|---|---|---|
| EP | 1 441 213 A1 | 7/2004 |
| EP | 1 443 318 A1 | 8/2004 |
| EP | 1 643 234 | 4/2006 |
| JP | 4127002 | 4/1992 |
| JP | 2004233353 | 8/2004 |
| JP | 2004233356 | 8/2004 |
| JP | 2005257687 | 9/2005 |
| WO | WO 01/81896 A1 * | 11/2001 |
| WO | WO 02/35580 A2 | 5/2002 |

OTHER PUBLICATIONS

Durkop et al., Title: "Properties and Applications of High-Mobility Semiconducting Nanotubes", J. Physics: Condens. Matter 16, (2004), pp. R553-R580.

(Continued)

*Primary Examiner* — Robert T. Crow (57) ABSTRACT

The invention provides an apparatus and method for sequencing and identifying a biopolymer. The invention provides a first electrode, a second electrode, a first gate electrode, a second gate electrode, a gate voltage source and a potential means. The gate electrodes may be ramped by a voltage source to search and determine a resonance level between the first electrode, biopolymer and second electrode. The potential means that is in electrical connection with the first electrode and the second electrode is maintained at a fixed voltage. A method of biopolymer sequencing and identification is also disclosed.

15 Claims, 5 Drawing Sheets

(56) References Cited

OTHER PUBLICATIONS

Japan Patent Office, Office Action dated Feb. 23, 2009.
Akeson, et al. "Microsecond Time-Scale Discrimination Among Polycytidylic Acid, Polyadenylic Acid, and Polyuridylic Acid as Homopolymers or as Segments Within Single RNA Molecules", Biophysical Journal, vol. 77, Dec. 1999, p. 3227-3233.

Kasianowicz, et al. "Characterization of individual polynucleotide molecules using a membrane channel", Proc. Natl. Acad. Sci. USA, vol. 93, p. 13770-13773, Nov. 1996.

Li, et al. "Ion-beam sculpting at nanometre length scales", Nature, vol. 412, Jul. 12, 2001.

* cited by examiner

BIOPOLYMER RESONANT TUNNELING WITH A GATE VOLTAGE SOURCE

CROSS REFERENCE TO RELATED APPLICATIONS

This application claims priority and is a continuation-in-part of application Ser. No. 10/957,378 filed on Sep. 30, 2004, entitled "Biopolymer Resonant Tunneling with a Gate Voltage Source".

TECHNICAL FIELD

The invention relates generally to the field of biopolymers and more particularly to an apparatus and method for biopolymer sequencing and identification using nanopore structures.

BACKGROUND

It has been demonstrated that a voltage gradient can drive single stranded polynucleotides through a nanometer diameter transmembrane channel, or nanopore. Kasianowicz, J. J. et al., Proc. Natl. Acad. Sci. USA 93, 13770-13773 (1996). During the translocation process, the extended polynucleotide molecules will block a substantial portion of the otherwise open nanopore channel. This blockage leads to a decrease in the ionic current flow of the buffer solution through the nanopore during the polynucleotide translocation. By measuring the magnitude of the reduced ionic current flow during translocation, the passage of a single polynucleotide can be monitored by recording the translocation duration and blockage current, yielding plots with characteristic sensing patterns. Theoretically, by controlling translocation conditions, the lengths of individual polynucleotide molecules can be determined from the calibrated translocation time. In addition, theoretically, the differing physical and chemical properties of the individual bases comprising the polynucleotide strand generate a measurable and reproducible modulation of the blockage current that allows an identification of the specific base sequence of the translocating polynucleotide. Kasianowicz, J. J. et al., Proc. Natl. Acad. Sci. USA 93, 13770-13773 (1996); Akeson, M. et al., Biophys. J. 77, 3227-3233 (1999). This method has the fundamental problem of measurement of very small currents at adequate bandwidth to supply the single-base resolution. It also is unclear if the very nature of the nanopore channel has the ability to provide adequate levels of specificity to distinguish one base from another.

Another means of detecting a polynucleotide translocating a nanopore has been proposed. It is based on quantum mechanical tunneling currents through the proximal base of the translocating strand as it passes between a pair of metal electrodes placed adjacent to the nanopore on the same surface of the underlying substrate. Measuring the magnitude of the tunneling current would be an electronic method for detecting the presence of a translocating molecule, and if the conditions were adequately controlled and the measurements sufficiently sensitive, the sequence of constituent bases could be determined. One of the primary motivations for this approach is that typical tunneling currents in scanning tunneling microscopes are on the order of 1-10 nanoamps. This is two to three orders of magnitude larger than the ionic currents observed during polymer translocation of 2 nanometer nanopores. However, it is well known that the tunneling current has an exponential dependence upon the height and width of the quantum mechanical potential barrier to the tunneling process. This dependence implies an extreme sensitivity to the precise location in the nanopore of the translocating molecule. Both steric attributes and physical proximity to the tunneling electrode could cause changes in the magnitude of the tunneling current which would be far in excess of the innate differences expected between different base types under ideal conditions. For this reason, it is difficult to expect this simplest tunneling configuration to have the specificity required to perform sequencing.

Recently, it was proposed that to adequately differentiate the bases via tunneling current, it is necessary to identify the internal energy level structure of each individual base as it translocates the pore. This can be accomplished with a structure that has the two electrodes comprising metal rings surrounding the nanopore and on opposite sides of the underlying substrate. As the biopolymer translocates the pore, the tunneling voltage applied between the two electrodes is periodically ramped at a rate that is substantially faster than the rate at which a single nucleotide passes through the pore channel. For the base near the center of the channel, the tunneling current undergoes a series of distinct peaks, each of which corresponds to a matching of the electrode energy levels with the relative internal energy levels of the specific bases. This tunneling enhancement is the well-known phenomenon of resonant quantum tunneling. The pattern of resonant peaks measured for each base is compared to a library of base spectra, and the sequence of bases identified. The reason that this resonant tunneling measurement modality requires a particular electrode arrangement is because specific spatial requirements must be satisfied to effect efficient resonant quantum tunneling. One particular problem with this resonant tunneling process is the fact that the biopolymer may take a variety of spatial positions in the nanopore as it translocates and is characterized. This variability in position of the molecule relative to the tunneling electrodes causes variability in the associated tunneling potentials. As will be described, this variability in the tunneling potentials translates into variability in the required applied voltage necessary to achieve the resonance condition yielding efficient resonant quantum tunneling and thus a smearing of the measured spectra results. Therefore, there is a need for new techniques and methodologies that can eliminate this smearing effect.

SUMMARY OF THE INVENTION

The invention provides an apparatus and method for characterizing and sequencing biopolymers. The apparatus comprises a first ring electrode, a second ring electrode adjacent to the first ring electrode, a potential means in electrical connection with the first ring electrode and the second ring electrode, a gate electrode, and a gate voltage source in electrical connection with the gate electrode. The gate voltage source is designed for providing a potential to the gate electrode for scanning the energy levels of a portion of a biopolymer translocating a nanopore. The nanopore is positioned adjacent to the first ring electrode and the second ring electrode and allows a biopolymer to be characterized and/or sequenced. The potential means is in electrical connection with the first ring electrode and the second ring electrode for applying a fixed potential from the first ring electrode, through a portion of the biopolymer in the nanopore to the second ring electrode.

The invention also provides a method for identifying a biopolymer translocating through a nanopore, comprising applying a ramping electrical potential from a gate voltage source across a gate electrode to identify a portion of the biopolymer positioned in the nanopore. A fixed potential may also be applied to the first ring electrode and the second ring electrode.

DETAILED DESCRIPTION OF THE INVENTION

Figure 1:
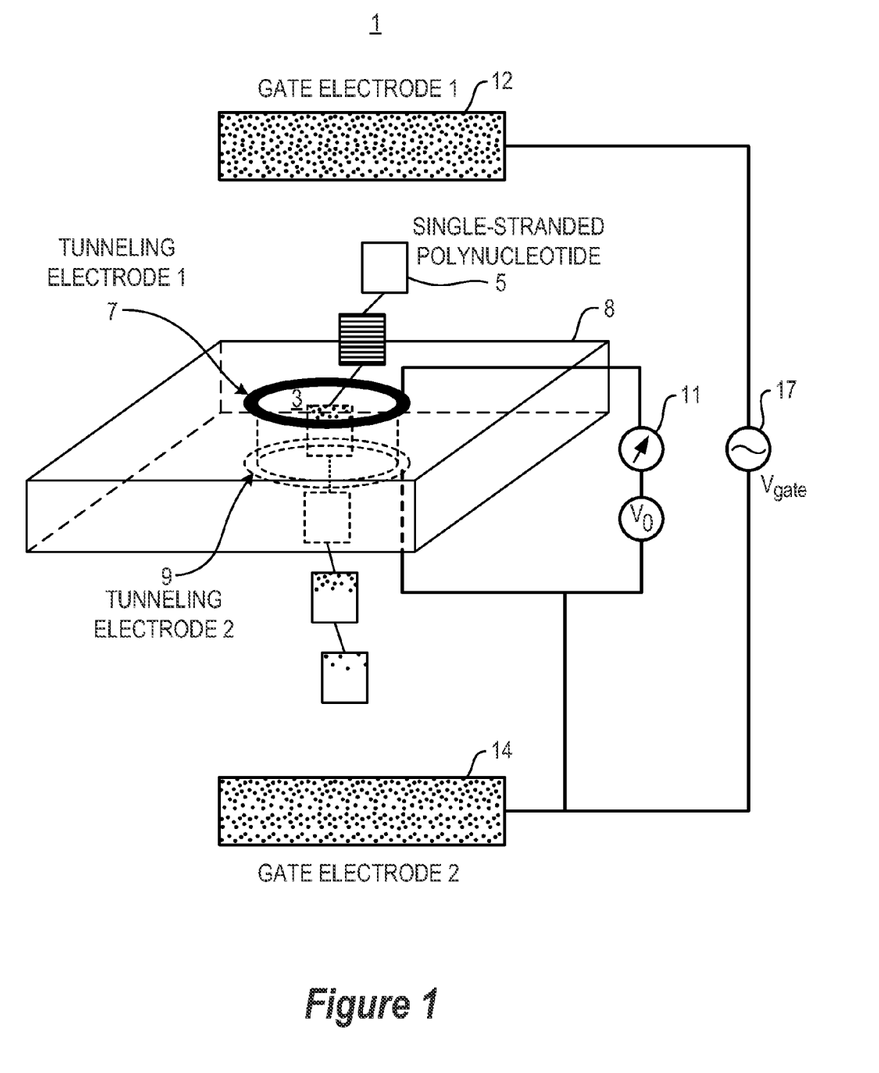
FIG. 1 shows a general perspective view of an embodiment of the present invention.
Figure 2:
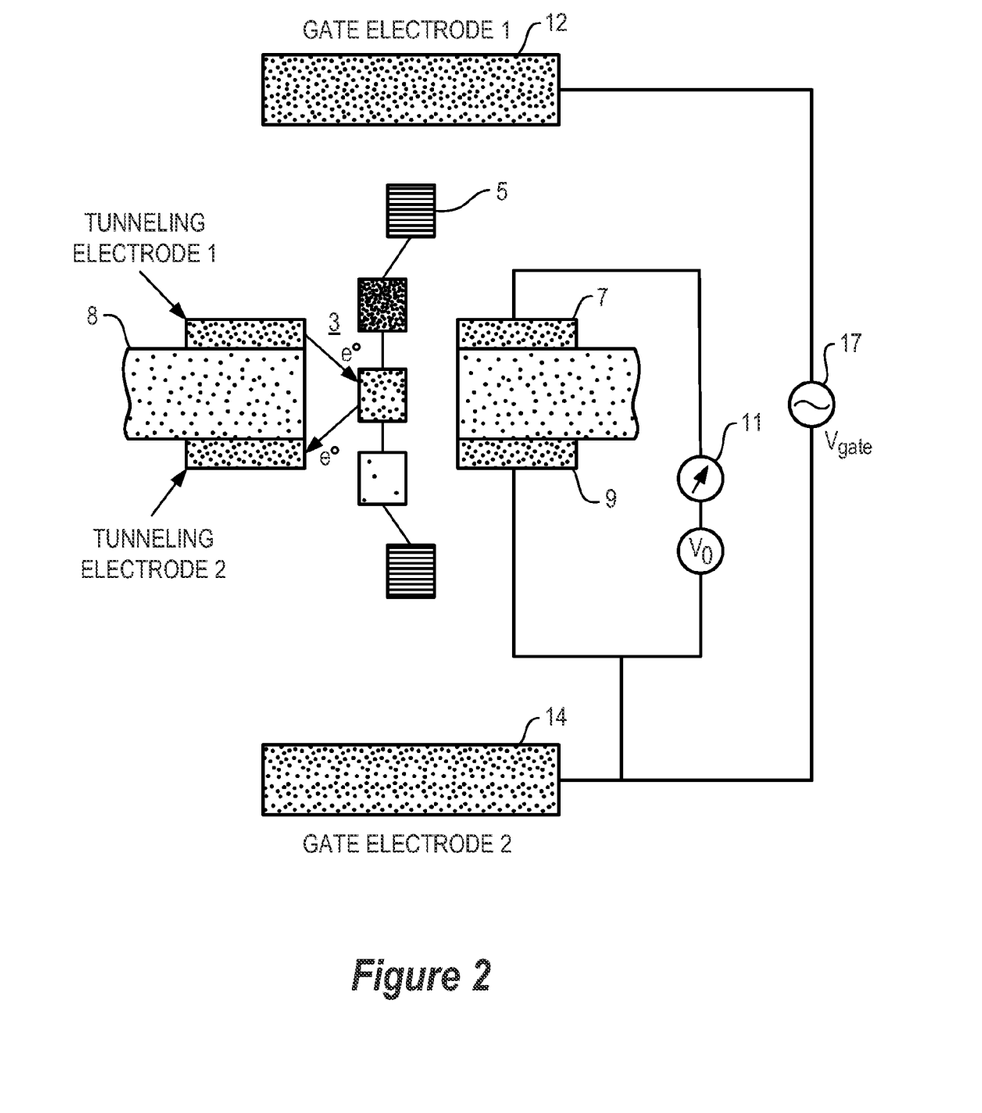
FIG. 2 shows a cross sectional view of the same embodiment of the present invention.
Figure 3:
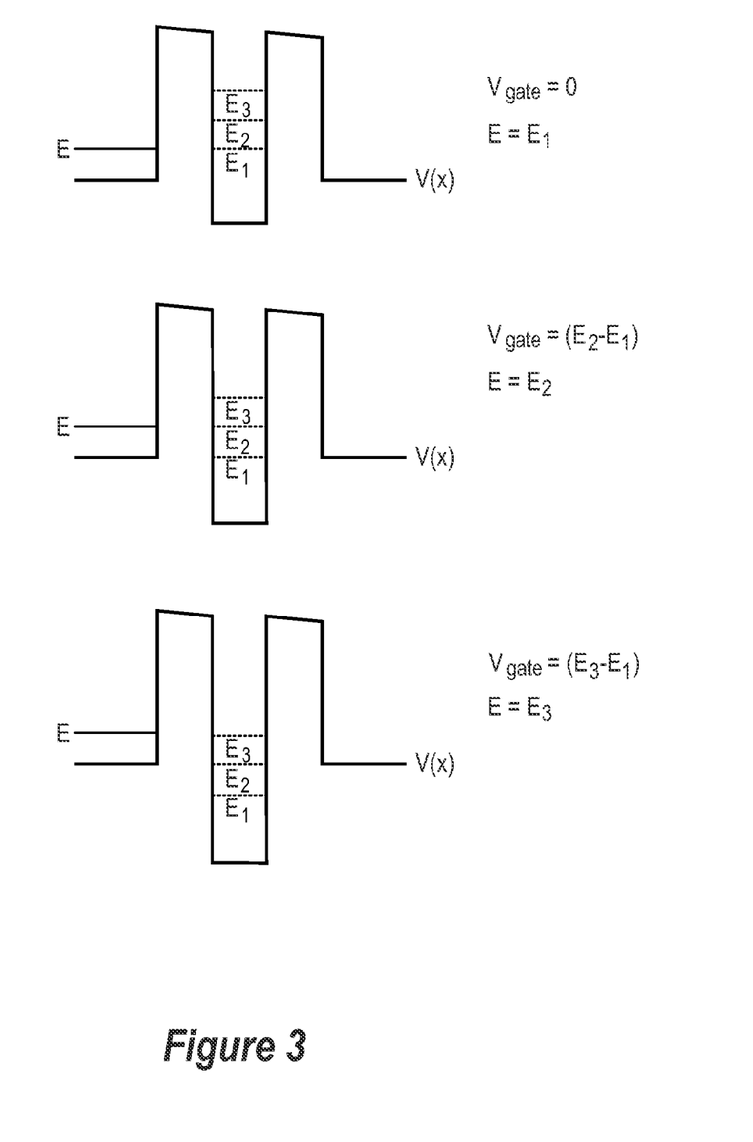
FIG. 3 shows the general energy wells and how they may be adjusted using the present invention.

Referring now to FIGS. 1-3, the present invention provides a biopolymer identification apparatus 1 that is capable of identifying and/or sequencing a biopolymer 5. The biopolymer identification apparatus 1 comprises a first electrode 7, a second electrode 9, a first gate electrode 12, a second gate electrode 14 and a potential means 11. In certain embodiments only a single gate electrode 12 may be employed. In either case, a gate voltage source 17 is employed with the first gate electrode 12 and/or second gate electrode 14. The gate voltage source 17 is in electrical connection with the first gate electrode 12 and/or the second gate electrode 14 to supply a ramping potential to identify and/or characterize a portion of a biopolymer 5 translocating a nanopore 3.

Each of the first and second electrodes may be ring shaped. The first electrode 7 and the second electrode 9 are electrically connected to the potential means 11, a first gate electrode 12 and a second gate electrode 14. The first gate electrode 12 and the second gate electrode 14 are electrically connected to the gate voltage source 17. The first electrode 7 is adjacent to the second electrode 9, the first gate electrode 12 and the second gate electrode 14. In certain embodiments the first electrode 7 and the second electrode 9 are disposed between the first gate electrode 12 and the second gate electrode 14. The nanopore 3 may pass through the first electrode 7 and the second electrode 9. However, this is not a requirement of the invention. In the case that the optional substrate 8 is employed, the nanopore 3 may also pass through the optional substrate 8. The nanopore 3 is designed for receiving a biopolymer 5. The biopolymer 5 may or may not be translocating through the nanopore 3. When the optional substrate 8 is employed, the first electrode 7 and the second electrode 9 may be deposited on the substrate, or may comprise a portion of the optional substrate 8. In this embodiment of the invention, the nanopore 3 also passes through the optional substrate 8. The first gate electrode 12 and/or the second gate electrode 14 may stand alone or comprise a portion of one or more optional substrates (substrates not shown in FIGS.).

The biopolymer 5 may comprise a variety of shapes, sizes and materials. The shape or size of the molecule is not important, but it must be capable of translocation through the nanopore 3. For instance, both single stranded and double stranded RNA, DNA, and nucleic acids. In addition, the biopolymer 5 may comprise groups or functional groups that are charged. Furthermore, metals or materials may be added, doped or intercalated into the biopolymer 5. These added materials provide a net dipole, a charge or allow for conductivity through the biomolecule. The material of the biopolymer must allow for electrical tunneling between the electrodes.

The first electrode 7 may comprise a variety of electrically conductive materials. Such materials comprise electrically conductive metals and alloys of tin, copper, zinc, iron, magnesium, cobalt, nickel, and vanadium. Other materials well known in the art that provide for electrical conduction may also be employed. When the first electrode 7 is deposited on or comprises a portion of the optional substrate 8, it may be positioned in any location relative to the second electrode 9. It must be positioned in such a manner that a potential can be established between the first electrode 7 and the second electrode 9. In addition, the biopolymer 5 must be positioned sufficiently close so that a portion of it may be identified or sequenced. In other words, the first electrode 7, the second electrode 9, the first gate electrode 12 and the second gate electrode 14, must be spaced and positioned in such a way that the biopolymer 5 may be identified or sequenced. This should not be interpreted to mean that the embodiment shown in the figures in any way limits the scope of the invention. The first electrode 7 may be designed in a variety of shapes and sizes. Other electrode shapes well known in the art may be employed. However, the design must be capable of establishing a fixed potential across the first electrode 7, the nanopore 3 and the second electrode 9. In addition, the first gate electrode 12 and the second gate electrode 14 are in electrical connection with the gate voltage source 17 for applying a ramped voltage to them.

All the electrodes may comprise the same or similar materials as discussed and disclosed above. As discussed above, the shape, size and positioning of the gate electrodes 12 and 14 may be altered relative to the first electrode 7, the second electrode 9 and the nanopore 3.

The optional substrate 8 may comprise a variety of materials known in the art for designing substrates and nanopores. The optional substrate 8 may or may not comprise a solid material. For instance, the optional substrate 8 may comprise a mesh, wire, or other material from which a nanopore may be constructed. Such materials may comprise silicon, silica, solid-state materials such as $Si_3N_4$ carbon based materials, plastics, metals, or other materials known in the art for etching or fabricating semiconductor or electrically conducting materials. The optional substrate 8 may comprise various shapes and sizes. However, it must be large enough and of sufficient width to be capable of forming the nanopore 3 through it.

The nanopore 3 may be positioned anywhere on/through the optional substrate 8. As describe above, the nanopore 3 may also be established by the spacing between the first electrode 7 and the second electrode 9 (in a planar or non planar arrangement). When the substrate 8 is employed, it should be positioned adjacent to the first electrode 7, the second electrode 9, the first gate electrode 12 and the second gate electrode 14. The nanopore may range in size from 1 nm to as large as 300 nm. In most cases, effective nanopores for identifying and sequencing biopolymers would be in the range of around 2-20 nm. These size nanopores are just large enough to allow for translocation of a biopolymer. The nanopore 3 may be established using any methods well known in the art. For instance, the nanopore 3 may be sculpted in the optional substrate 8, using argon ion beam sputtering, etching, photolithography, or other methods and techniques well known in the art.

The first gate electrode 12 and the second gate electrode 14 are designed for ramping the voltage so that the various energy levels of the translocating biopolymer 5 can be scanned. Resonance is achieved when an energy level of the biopolymer 5 coincides with the energy of an electron in the electrode 7 as shown schematically in FIG. 3. Resonance provides reduced electrical resistance between the first electrode 7, the second electrode 9 and the biopolymer 5. By ramping the gate voltage source 17, the energy levels are scanned and the sequence of the biopolymer 5 can be determined by matching the measured tunneling current spectrum with a catalogue of spectra for the individual translocating biopolymer segments. In addition, by fixing the potential means 11 that is in electrical connection with the first electrode 7 and the second electrode 9, and scanning the various energy levels with the first gate electrode 12 and the second gate electrode 14 using the gate voltage source 17, the "smearing out" of the various sensing patterns can be avoided. In other words, this technique allows for the clean separation of characteristic sensing patterns and peaks. The first gate electrode 12 and the second gate electrode 14 may be positioned anywhere about the nanopore 3. However, in most situations the first gate electrode 12 and the second gate electrode 14 may be positioned adjacent to the first electrode 7, the biopolymer 3, and the second electrode 9. A variety of gate electrodes may be employed with the present invention. In no way should the described embodiments limit the scope of the invention.

The gate voltage source 17 may be positioned anywhere relative to the optional substrate 8, the nanopore 3, the first electrode 7 and the second electrode 9. The gate voltage source 17 is designed for ramping the voltage applied to the first gate electrode 12 and the second gate electrode 14. The potential means 11 should be capable of establishing a fixed voltage between the first electrode 7 and the second electrode 9. A variety of gate voltage sources 17 and potential means 11 may be employed with the present invention. For a reference and figures regarding contrasting inventions that ramp the first electrode 7 and the second electrode 9 by only the potential means 11, please see U.S. Ser. No. 10/352,675 entitled "Apparatus and Method for Biopolymer Identification During Translocation Through a Nanopore" by Curt Flory.

The potential means 11 may be positioned anywhere relative to the optional substrate 8, the nanopore 3, the first electrode 7 and the second electrode 9. The potential means 11 should be capable of establishing a fixed voltage between the first electrode 7 and the second electrode 9. A variety of potential means 11 may be employed with the present invention.

An optional means for signal detection may be employed to detect the signal produced from the biopolymer 5, the gate electrodes 12 and 14, the electrodes 7 and 9 and the potential means 11. The means for signal detection may comprise any of a number of devices known in the art. Basically, the device should be capable of data storage to store the spectrum and data determined from the biopolymer 5. In addition, this device should also be able to compare this data and spectrum to a number of previously determined and calibrated spectrums to determine the unknown spectrum or chemical components.

Figure 4:
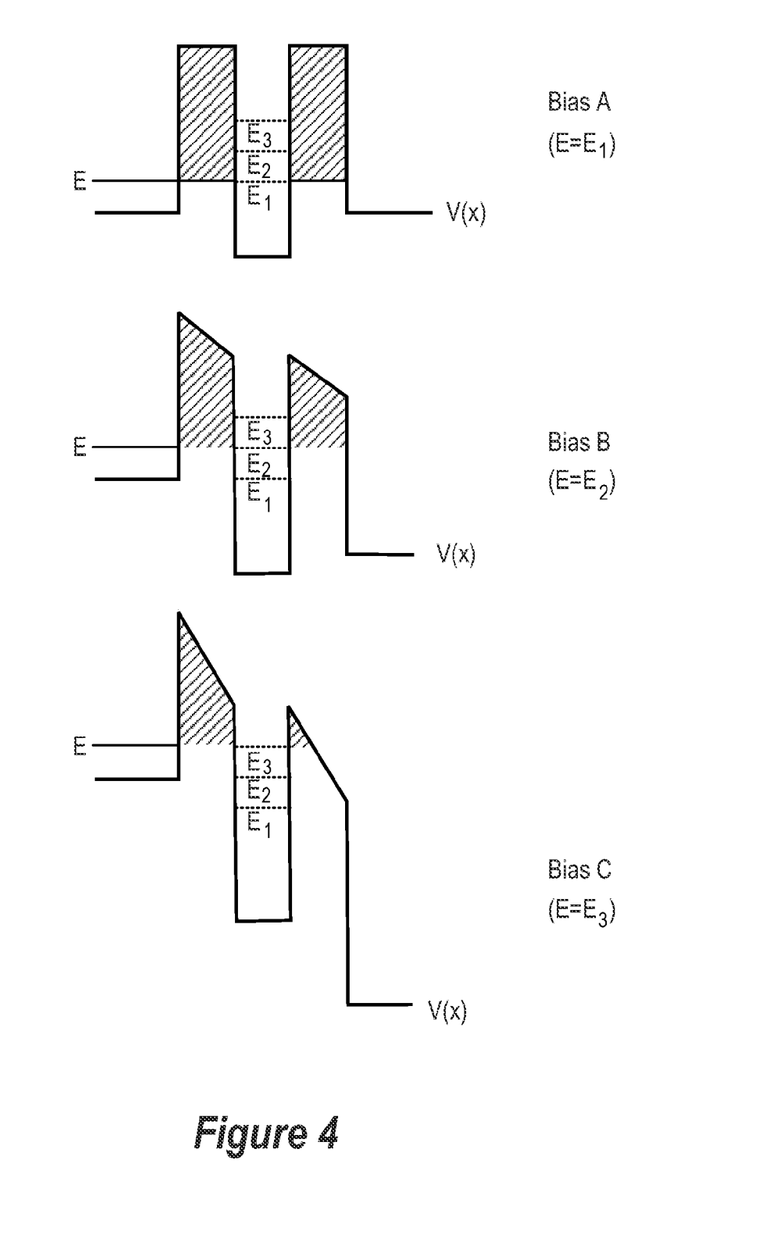
FIG. 4 shows the wells and energy levels in a fixed spatial position.

As mentioned above, the previous resonant tunneling approach to biopolymer sequencing and identification has an artifact that causes the peaks in the measured nucleotide spectra to spread, leading to a lower signal-to-noise ratio than might otherwise be achieved. This effect originates in the requirement that for maximal resonant quantum tunneling, two conditions must be met. The first condition is that the incident electron energy and the nucleotide bound state energy match. The second condition is that the two tunneling barriers must have equal strengths, where the barrier strength, B, is defined by $$B = \int_{x_1}^{x_2} \sqrt{V(x) - E}\, dx \quad (1)$$

where $x_1(x_2)$ is the initial (final) point of the 1-d potential barrier described by $V(x)$. The difficulty arises from the fact that for different tunneling bias voltages, the two tunneling barriers have their strengths equalized at different positions during the nucleotide translocation process. (Also, reciprocally, for different positions during the translocation process, the incident electron energy and nucleotide bound state energy are matched by different tunneling bias voltages). This is easily illustrated in FIG. 3, which shows the effective tunneling barriers shaded to highlight the different barrier mismatches for different applied tunneling bias voltages when the nucleotide position is fixed in space (in this case, equidistant to both tunneling electrodes). It becomes clear that to have the barrier strengths equalized for each of the bias voltages, the barrier spatial widths must have different ratios, which corresponds to different spatial positions for the nucleotide during the translocation process. This is illustrated in FIG. 4. Therefore, the dominant signal contribution from each particular component of the nucleotide spectrum occurs over a particular portion of the translocation trajectory during which the tunneling barriers are roughly symmetrized for that specific voltage. It is also seen from the figures that the ratio of the voltage drops across each of the barriers changes as their widths change. This means that the tunneling voltage at which resonance occurs also depends upon the relative spatial location of the nucleotide with respect to the electrodes. Although the dominant contribution to each spectral component occurs when the barriers are precisely symmetrized, there are subdominant contributions from the contiguous parts of the trajectory where the barriers are not far from symmetry. These contributions that are generated over a localized spatial distribution, by the arguments shown above, cause the spectral component to be distributed over a nonzero tunneling voltage range. This spreading of the spectral components is the effect to be eliminated by the present invention.

Figure 5:
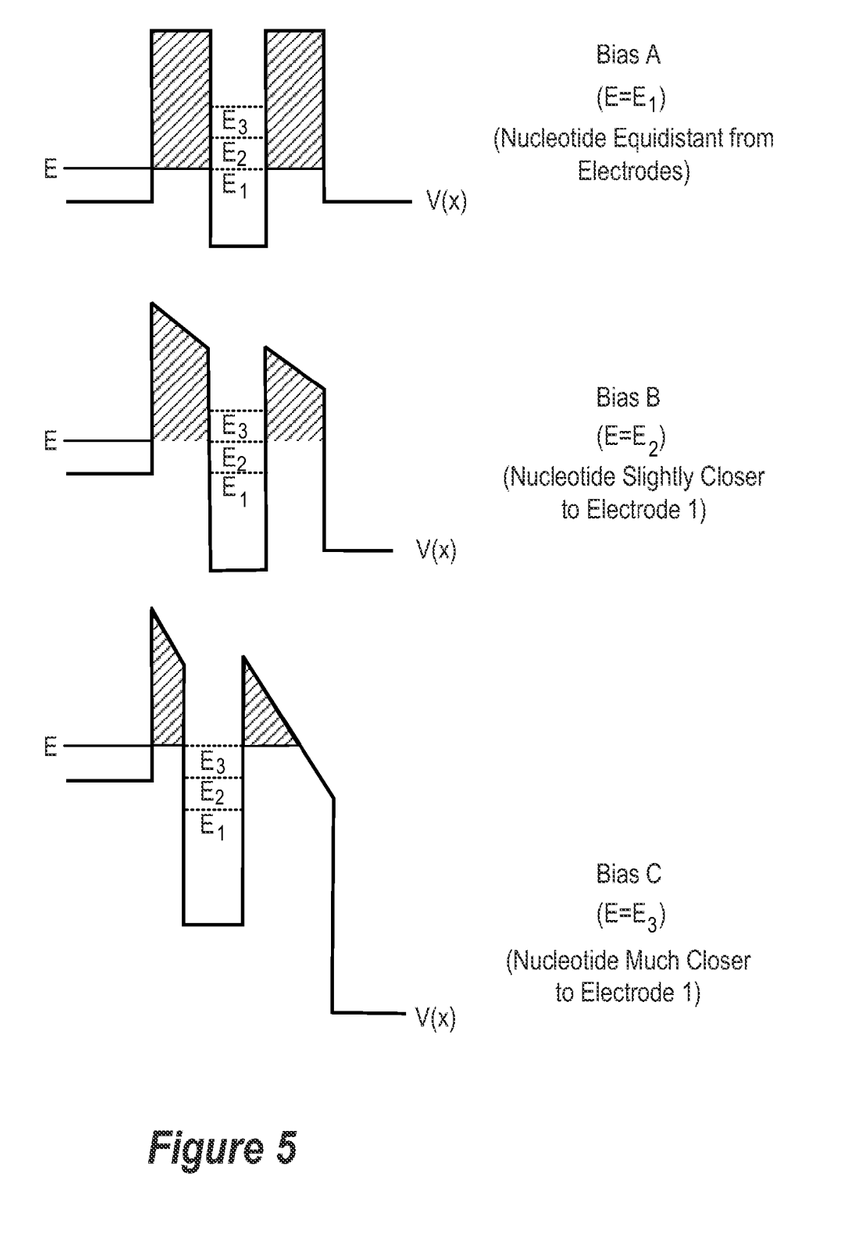
FIG. 5 shows the wells and energy levels as the spatial position varies.

FIGS. 1 and 2 show an embodiment of the present invention. The invention comprises one or more gate electrodes that may be positioned adjacent to the first electrode 7 and the second electrode 9. The gate electrodes 12 and 14 are designed to provide the time dependent gate voltage that scans the spectrum of the translocating molecules. The tunneling voltage applied between the tunneling electrodes is held to a small fixed value $V_0$. The variations in the measured tunneling current in this circuit are due to the resonant quantum tunneling between these electrodes and the translocating bases as the varying gate voltage Vgate, causes the base resonance energies to sequentially match the energy of the electrons in the electrodes. This process is shown in FIG. 5. The base resonance energies are caused to align with the electrode electron energy at values that are independent of the position of the base between the electrodes (i.e. tunneling barrier widths). Therefore, as the base translocates the region between the tunneling electrodes, and the gate voltage is continually cycled at a period substantially shorter than the translocation time, an invariant resonant tunneling spectrum is measured during each cycle, with the preponderance of the current being measured during that portion of the trajectory when the tunneling barriers are equal. The spectral distribution (but not the magnitudes) of the contribution from each of these cycles is independent of the spatial position, and thus the "spectral spreading effect" inherent in the previous measurement modality is minimized.

Typical exemplary operating values for this device can be based upon measurements using the present non-tunneling nanopore devices. The fixed tunneling voltage applied between the tunneling electrodes should be in the nominal range of 0.1-0.2 volts. This range, however, is not restricted and may be much broader depending upon the application. The period of the time-varying gate voltage should be much shorter than the translocation time of an individual base, currently estimated to be on the order of a microsecond. Thus, the frequency of the gate voltage should be greater than about 10 MHz. The amplitude of this voltage should be adequate to scan an appreciable segment of the internal energy spectrum of the translocating bases. Typical amplitudes for this voltage should be in the range of from 0.1-1.0 volts, although not restricted to this range.

The electrodes for this device may comprise a variety of materials as discussed above. To minimize the shorting effect of the ionic fluids on the electrodes and/or gate electrodes, the electrodes may be encased in a thin insulating film that blocks the ion conduction, but has little effect on the tunneling currents during resonant quantum tunneling. One possible embodiment would be the creation of a layer of native oxide for the electrode metal. Another would be the deposition of a thin insulating layer over the tunneling electrodes during the fabrication process. These insulating layers may comprise any number of typical materials used during this process. For instance, this may comprise silicon dioxide or photoresist. The deposition of the insulating layer may advantageously occur by atomic layer deposition.

The method of the present invention will now be discussed. The method of the present invention comprises applying a ramping electrical potential across one or more gate electrodes, to identify a portion of the biopolymer positioned in the nanopore. In addition, the first electrode 7 and the second electrode 9 may be maintained at a fixed voltage by the potential means 11. This allows for scanning of the energy levels by the first gate electrode 12 and the second gate electrode 14 and gate voltage source 17.

Initially, the biopolymer 5 is allowed to translocate through the nanopore 3. In addition the biopolymer 3 passes between the first electrode 7 and the second electrode 9. These electrodes are maintained at a fixed potential by the potential means 11. At the same time, one or more gate electrodes may be employed that are adjacent to the first electrode 7 and the second electrode 9. The first gate electrode 12 and the second gate electrode 14 may then be ramped by voltage source 17 in order to scan the internal energy spectrum of the portion of the biopolymer 5 positioned in the nanopore 3 between the first electrode 7 and the second electrode 9. The signal that is produced is compared to a pre-determined spectrum determined for each of the particular nucleotide bases. Each of the main portions of the signal are compared and then the actual nucleotide base can be determined. This is then repeated for each of the bases that pass through the nanopore 3 and between the first electrode 7 and the second electrode 9.

Example 1

The present invention may be fabricated using various techniques and tools known in the art. The invention should not be interpreted to be limited to this example. The example is provided for illustration purposes. The nanopore can be made in a thin (500 nM) freestanding silicon nitride (SiN3) membrane supported on a silicon frame. Using a Focused Ion Beam (FIB) machine, a single initial pore of roughly 500 nm diameter may be created in the membrane. Then, illumination of the pore region with a beam of 3 KeV argon ions sputters material and slowly closes the hole to the desired dimension of roughly 2 nM in diameter (See Li et al., "Ion Beam Sculpting at Nanometer Length Scales", Nature, 412: 166-169, 2001). Metal electrodes are formed by evaporation or other deposition means on the opposing surfaces of the SiN3 membrane. A voltage source is connected to the tunneling electrode to maintain a fixed voltage. Wire bonding to the tunneling electrodes allows connection to the voltage source and the tunneling current system. In one embodiment, the gate electrodes can be comprised of silver-chloride or similar type materials or metals. These electrodes are then immersed in a buffer fluid on opposite sides of the membrane supporting the nanopore. The gate voltage is applied to the gate electrodes. The bias is applied using an AC source with the modest requirement of roughly 3-5 volts at 30-50 MHz. The tunneling currents are expected to be in the nanoamp range, and can be measured using a commercially available patch-clamp amplifier and head-stage (Axopatch 200B and CV203BU, Axon Instruments, Foster City, Calif.).

We claim:

1. An apparatus for detecting a biopolymer in a nanopore, comprising:
    (a) a first ring electrode;
    (b) a second ring electrode adjacent to the first ring electrode;
    (c) a first gate electrode in electrical connection with the first ring electrode and the second ring electrode for scanning the energy spectrum of the biopolymer;
    (d) a second gate electrode in electrical connection with the first ring electrode and the second ring electrode, the second gate electrode arranged for scanning the energy spectrum of the biopolymer;
    (e) a nanopore adjacent to the first ring electrode and the second ring electrode and positioned to allow the biopolymer to be positioned in the nanopore and between the first ring electrode and the second ring electrode;
    (f) a first voltage source in electrical connection with the first ring electrode and the second ring electrode, the first voltage source configured to apply a fixed potential from the first ring electrode, through a portion of the biopolymer in the nanopore, to the second ring electrode to produce a signal indicative of the portion of the biopolymer; and
    (g) a second voltage source in electrical connection with the first gate electrode and the second gate electrode, the second voltage source configured to apply a periodic voltage to the first gate electrode and the second gate electrode and having a period that is substantially less than a translocation time of an individual base.

2. The apparatus of claim 1, further comprising a substrate for positioning the first ring electrode and the second ring electrode.

3. The apparatus of claim 1, further comprising at least a first substrate for positioning the first ring electrode.

4. The apparatus of claim 1, further comprising at least a second substrate for positioning the second ring electrode.

5. The apparatus of claim 1, further comprising at least a first substrate for positioning a nanopore.

6. The apparatus of claim 1, further comprising a signal detecting device arranged to detect the signal produced from the portion of the biopolymer.

7. The apparatus of claim 1, wherein the biopolymer is a charged polymer.

8. The apparatus of claim 1, wherein the biopolymer is selected from the group consisting of carbohydrates, proteins, nucleic acids, lipids, glycans, polynucleotides, proteoglycans, and polypeptides.

9. An apparatus for detecting a biopolymer translocating a nanopore, comprising:
   (a) first electrode having a first nanopore;
   (b) second electrode adjacent to the first electrode having a second nanopore wherein the first nanopore of the first electrode is positioned with the second nanopore of the second electrode so that the biopolymer may translocate through the first nanopore and the second nanopore;
   (c) a gate electrode in electrical connection with the first electrode and the second electrode, the gate electrode arranged and configured for scanning the energy levels of the biopolymer; and
   (d) a first voltage source connected to the first electrode and the second electrode, the first voltage source configured to apply a fixed potential from the first electrode through a portion of the biopolymer to the second electrode to produce a detectable signal indicative of a portion of the biopolymer translocating the first nanopore and the second nanopore; and
   (e) a second voltage source in electrical connection with the gate electrode, the second voltage source configured to apply a periodic voltage to the gate electrode having a period substantially less than a translocation time of an individual base.

10. An apparatus as recited in claim 9, wherein the nanopore of the first electrode has a center point and the nanopore of the second electrode has a center point and wherein the center point of the first electrode is positioned coaxially with the center point of the second electrode.

11. An apparatus as recited in claim 10, wherein the first electrode is positioned above said second electrode.

12. An apparatus as recited in claim 9, further comprising a substrate for positioning the first electrode and the second electrode.

13. An apparatus as recited in claim 9, further comprising a second substrate for positioning the second electrode.

14. An apparatus for detecting a portion of a biopolymer translocating a nanopore, comprising:
   (a) a first electrode;
   (b) a second electrode spaced from the first electrode to define a nanopore between the first electrode and the second electrode, the nanopore being designed for receiving a translocating biopolymer, the first electrode being in electrical connection with the second electrode;
   (c) a gate electrode in electrical connection with the first electrode and the second electrode, the gate electrode arranged for scanning the energy levels of the biopolymer;
   (d) a first voltage source for electrically connecting the first electrode and the second electrode, the first voltage source configured to apply a fixed potential across the biopolymer to the second electrode to produce a modulated signal that is indicative of a portion of the biopolymer translocating the nanopore; and
   (e) a second voltage source in electrical connection with the gate electrode, the second voltage source configured to apply a periodic voltage to the gate electrode, having a period substantially less than a translocation time of an individual base.

15. An apparatus as recited in claim 14, wherein the biopolymer is translocated in a stepwise fashion though the nanopore defined between the first electrode and the second electrode.

* * * * *

UNITED STATES PATENT AND TRADEMARK OFFICE
CERTIFICATE OF CORRECTION

| | | |
|---|---|---|
| PATENT NO. | : 8,563,237 B2 | Page 1 of 1 |
| APPLICATION NO. | : 10/996846 | |
| DATED | : October 22, 2013 | |
| INVENTOR(S) | : Curt A. Flory et al. | |

It is certified that error appears in the above-identified patent and that said Letters Patent is hereby corrected as shown below:

In the Claims:

In column 10, line 32, In Claim 15, delete "though" and insert -- through --, therefor.

Signed and Sealed this
First Day of April, 2014

Michelle K. Lee
*Deputy Director of the United States Patent and Trademark Office*